United States Patent [19]

Swann et al.

[11] Patent Number: 5,472,566
[45] Date of Patent: Dec. 5, 1995

[54] SPECIMEN HOLDER AND APPARATUS FOR TWO-SIDED ION MILLING SYSTEM

[75] Inventors: Peter R. Swann, St. Johns, Antigua/Barbuda; Reza Alani, Pleasanton, Calif.

[73] Assignee: Gatan, Inc., Pleasanton, Calif.

[21] Appl. No.: 339,483

[22] Filed: Nov. 14, 1994

[51] Int. Cl.⁶ .................. H01L 21/00; H01L 21/306; B44C 1/22; C03C 15/00
[52] U.S. Cl. .................. 156/643.1; 156/626.1; 156/345; 216/66
[58] Field of Search .................. 156/345, 626.1, 156/643.1, 662.1; 204/192.33, 192.34, 192.37, 298.32, 298.36; 216/66, 79, 80

[56] References Cited

U.S. PATENT DOCUMENTS

| | | | |
|---|---|---|---|
| 4,128,765 | 12/1978 | Franks | 204/298.36 |
| 4,411,733 | 10/1983 | Macklin et al. | 204/298.36 |
| 5,009,743 | 4/1991 | Swann | 156/643 |
| 5,223,109 | 6/1993 | Itoh | 204/298.36 |

FOREIGN PATENT DOCUMENTS

| 141272 | 1/1989 | European Pat. Off. . |
|---|---|---|
| 267481 | 7/1990 | European Pat. Off. . |

OTHER PUBLICATIONS

E. A. Fischione Instruments, Inc. brochure—Model 3000 Ion Mill.
Alani et al, "Chemically Assisted Ion Beam Etching—A New Technique for TEM Specimen Preparation of Materials," reprinted from Materials Res. Soc. Symposium Proc., vol. 199.
Bal–Tec AG brochure—Rapid Ion Beam Milling System.
Technoorg Linda data sheet—Ion Beam Thinning Unit for TEM/Ion Beam Slop Cutting for SEM.

*Primary Examiner*—William Powell
*Attorney, Agent, or Firm*—Killworth, Gottman, Hagan & Schaeff

[57] ABSTRACT

An apparatus and a specimen holder adapted to permit simultaneous two-sided ion beam milling at very low angles of beam incidence, down to 0°, from both sides of the specimen is provided and includes a specimen holder for two-sided ion beam milling and a pedestal having at least one extending specimen support arm adapted to engage a peripheral edge of a specimen. The specimen is secured to the at least one specimen support arm, preferably, so as to permit ion beams to be directed at the first and second major surfaces of the specimen simultaneously at very low angles of incidence down to 0°. Both rapid milling as well as a reduction in artifacts provide high quality specimens for transmission electron microscopy analysis.

24 Claims, 5 Drawing Sheets

SPECIMEN HOLDER AND APPARATUS FOR TWO-SIDED ION MILLING SYSTEM

BACKGROUND OF THE INVENTION

The present invention relates to an ion beam milling apparatus and method including a specimen holder for the preparation of transmission electron microscope specimens, and more particularly to a specimen holder and method which permits two-sided milling at very low angles down to 0°.

Transmission electron microscopy is an important technique for studying the detailed microstructure of many materials. Improvements in the design and operation of electron microscopes have generated considerable interest in obtaining atomic resolution images of various materials. However, the preparation of specimens for atomic resolution transmission electron microscopy is demanding, requiring a final specimen which is very thin (i.e., <50 nm) and free from artifacts. Typically, specimen preparation involves initial slicing, sectioning, trepanning, and/or grinding operations to produce a relatively thin (100–200 μm) disk of approximately 3 mm diameter.

Ion beam milling systems have been used to prepare specimens of various materials including ceramics, semiconductors, metals, and combinations thereof for atomic resolution transmission electron microscopy. In such ion beam milling systems, such as the system disclosed in commonly-assigned U.S. Pat. No. 5,009,743, to Swann, specimens are mounted on holders and placed in the path of one or more ion beams. The ion beams gradually remove atoms from the surface of the specimen until a small perforation is formed in the center of the specimen. Generally, the area around the perforation is then thin enough (i.e., <50 nm) for atomic resolution analysis by a transmission electron microscope.

However, ion milling is a slow process. To increase the rate at which atoms are removed from the surface of the specimen, it is a common practice to mill the specimen at higher angles of from 15°–25° between the incident beam and the specimen surface. Such higher angles maximize the effects of the beam but may cause artifacts such as crystallographic imperfections and amorphous surface layers which result from the penetration of energetic ions and atoms into the surface of the specimen.

The total milling rate may also be increased through the use of two or more ion guns simultaneously from both sides of the specimen. Prior art specimen holders have been designed to accommodate high angle milling, milling from both sides, and specimen rotation to obtain more uniform thinning across the specimen surface. Such holders have included a pair of annular thin metallic plates, called clamping plates, having openings of a diameter just less than the diameter of a typical specimen (i.e., about 3 mm). The specimen is placed between the clamping plates concentrically within the annular openings. The entire assembly is then clamped together and mounted in an auxiliary holder to provide rotation.

Since ion beams are collimated and not focused, they are relatively broad in comparison to specimen size. Thus, in addition to striking the specimen, the ion beams strike the clamping plates as well as other parts of the auxiliary holder. This can result in the deposition of sputtered material from the clamping plates and auxiliary holder onto the specimen creating troublesome artifacts on the surface(s) of the specimen. The thinning of the clamping plates and auxiliary holder due to this sputtering necessitates frequent replacement.

Another problem with conventional clamping plates is that their thickness limits the minimum attainable milling angle for the specimen. This is because the clamping plates must have some mechanical strength, which requires that they have a certain minimum thickness. Clamping plates with somewhat greater thicknesses than that which is absolutely necessary are sometimes favored because they have a longer useful life, especially in view of the thinning which results from repeated use.

While higher milling angles produce more rapid milling of the specimen surface, ion milling at glancing angles of about 5° or less has become increasingly popular because it produces higher quality specimens and fewer artifacts, especially specimens composed of materials which are difficult to mill. For example, in some two-phase specimens, one phase is milled more rapidly than the other. Specimens milled at higher angles are of lower quality and include surface roughness, limited thin areas, and differential thinning rates for different constituents in the specimen; low angle milling overcomes many of these problems.

A major requirement for low angle ion milling is a specimen holder with an appropriate line-of-sight capability. That is, the specimen holder must permit one or more ion beams to be directed against the specimen at angles down to 0°. An example of a specimen holder having low angle milling capability is the holder disclosed in the above-mentioned U.S. Pat. No. 5,009,743. In that patent, specimens are seated on the top face of a pedestal, permitting one or more ion beams to be directed at one side of the specimen at milling angles down to 0°. The holder includes a raised lip on the upper surface of the pedestal to secure the specimen. However, such a holder does not permit two-sided milling or removal of any contaminants from the underside of the specimen. Further, the raised lip is milled away by the action of the ion beams, necessitating frequent replacement of the specimen holder.

Accordingly, the need still exists in this art for ion milling apparatuses including specimen holders which permit simultaneous two-sided ion beam milling at very low angles down to 0°.

SUMMARY OF THE INVENTION

The present invention meets that need by providing an apparatus and a specimen holder adapted to permit the simultaneous two-sided ion beam milling of a specimen at very low angles of beam incidence, down to 0°, from both sides of the specimen. This produces both rapid milling as well as reducing artifacts to provide high quality specimens for transmission electron microscopy analysis.

In accordance with one aspect of the present invention, a specimen holder for two-sided ion beam milling is provided and includes a pedestal having at least one extending specimen support arm adapted to engage a peripheral edge of a specimen and means for securing the specimen to the least one specimen support arm. Preferably, the specimen is secured to the support arm so as to permit ion beams to be directed at the first and second major surfaces of the specimen simultaneously at very low angles of incidence down to 0°. The support arm has a narrow profile such that at least a portion of the peripheral edge of the specimen remain unrestrained and spaced from the pedestal. The number of support arms may vary depending upon the type of specimen and the placement of the ion beam guns for milling, and there may be from one to a plurality or multiplicity of support arms for supporting the sample.

The specimen is secured to at least one support arm by seating the specimen in a recess in the support arm which engages the edge of the specimen. The depth of the recess is less than the height of the specimen. Securing means are provided to insure that the specimen remains in a fixed position during milling. In a preferred embodiment of the invention, such securing means comprises a wax, such as for example, a low melting point hydrocarbon wax. The wax is disposed in the recess in the support arm, and the specimen is secured by melting or softening the wax, seating the specimen, and then cooling the wax. The wax also provides an advantageous heat transfer medium to transfer heat from the specimen to the support arm. This reduces ion beam induced heat damage effects.

In another embodiment of the invention, the securing means is a clamp. The clamp may take one of several structural forms. In one form, the clamp includes a clamping surface for engaging a peripheral edge of the specimen, a post extending from the clamping surface, and a spring on the post for biasing the clamping surface against the specimen support arm. In another form, the clamp includes a clamping surface for engaging a peripheral edge of the specimen and a screw extending through the clamping surface for securing the clamping surface to the specimen support arm. In yet another form, the clamp includes a C-shaped clamp having a clamping surface for engaging the edge of the specimen and a base portion extending around and securing the clamp to the specimen support arm.

Preferably, the pedestal has a bore therethrough so that the milling process may be monitored, such as for example by impinging a beam of light on the specimen surface. The beam will pass through the bore in the pedestal and specimen as soon as the milling perforates the specimen and is detected by a suitable detector.

In a preferred form, the specimen support arm includes a first portion which extends laterally away from the pedestal, a second upstanding portion, and a third portion extending laterally toward the pedestal. The support arm includes a recess in the third portion thereof for engaging the edge of the specimen, with the depth of the recess being less than the height of the specimen.

The specimen holder of the present invention may be used in almost any ion milling system. However, in a preferred embodiment, an apparatus for two-sided ion beam milling is provided and includes a vacuum chamber and means for providing a vacuum within the chamber and a specimen holder within the chamber for holding a specimen to be milled. A plurality of ion guns are positioned within the chamber, with at least one of the guns positioned to provide an ion beam to a first side of the specimen and at least one other of the guns positioned to provide an ion beam to a second side of the specimen. The plurality of guns are adjustable to provide very low milling angles of incidence down to 0°.

The specimen holder of the present invention is adaptable for use in various ion milling systems and configurations. By providing line-of-sight access to both sides of the specimen surface through the use of narrow profile support arms, with at least a portion of the peripheral edge of the specimen remaining unrestrained, very low milling angles down to 0° are achieved and ion beam impingement on the specimen holder is minimized. Further, total milling rates are increased while specimen contamination is reduced.

The present invention also provides a method for the two-sided ion beam milling of specimens and includes the steps of providing a specimen having first and second major surfaces and a peripheral edge to be milled to a vacuum chamber and securing the specimen such that at least a portion of the peripheral edge remains unrestrained, evacuating the chamber to form a vacuum therein, and ion milling the specimen using a milling angle down to 0°. The method may also be used for simultaneously milling the specimen on both major surfaces thereof through the use of ion beam guns positioned on either side of the specimen. Optionally, the specimen may be rotated during milling thereof.

Accordingly, it is an object of the present invention to provide an ion milling apparatus and specimen holder adapted to permit two-sided ion beam milling at very low angles of beam incidence, down to 0°, from both sides of the specimen. This, and other features and advantages of the present invention, will become apparent from the following detailed description, the accompanying drawings, and the appended claims.

BRIEF DESCRIPTION OF THE DRAWINGS

FIG. 1b is a cross-sectional view of the specimen holder of FIG. 1a;

FIG. 2b is a cross-sectional view of the specimen holder of FIG. 2a;

DETAILED DESCRIPTION OF THE PREFERRED EMBODIMENTS

Figure 1A:
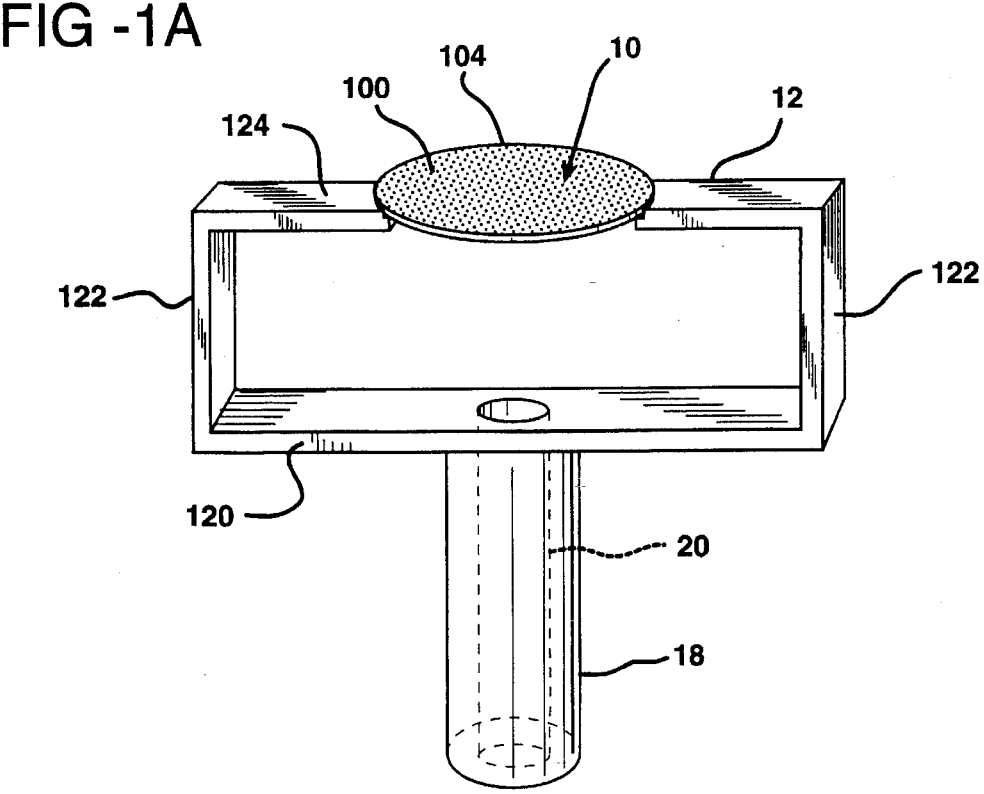
FIG. 1a is a perspective view of a two support arm embodiment of the present invention which secures the specimen with wax.
Figure 1B:
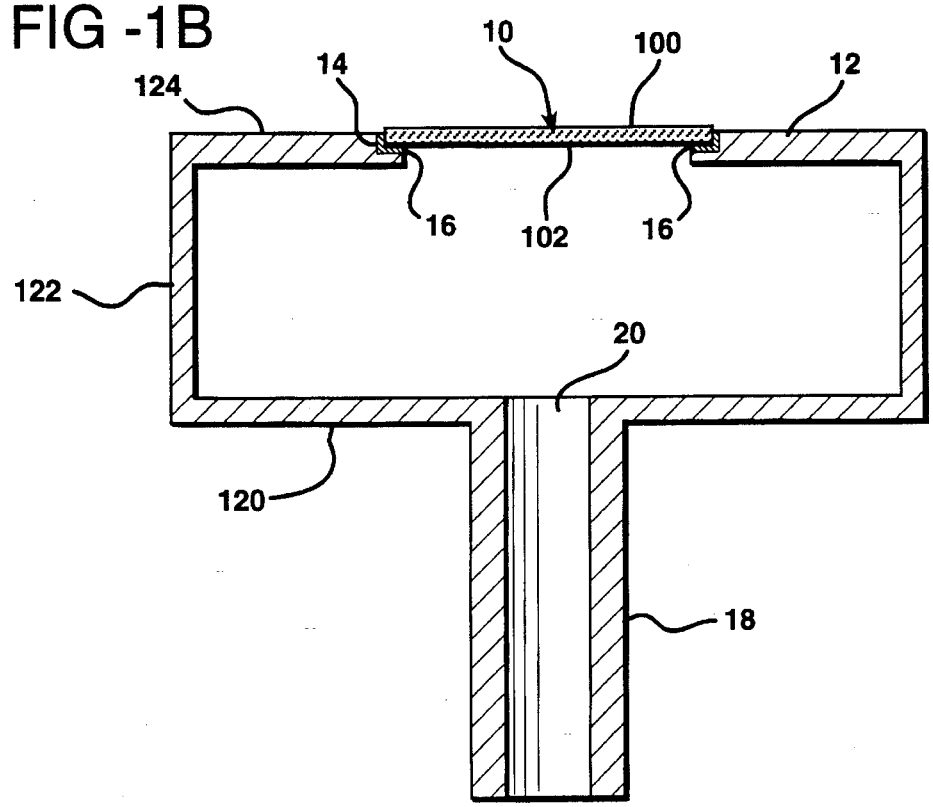

One embodiment of the specimen holder of the present invention having a pair of opposing support arms is illustrated in FIGS. 1a and 1b. As shown, specimen 10, having first and second major surfaces 100 and 102 and peripheral edge 104, is seated on support arms 12. As is typical in the art, specimen 10 is in the form of a circular disk having a diameter of approximately 3 mm. The support arms are spaced so that they define a gap therebetween of less than the diameter of specimen 10. Support arms 12 are mounted on or otherwise secured to upstanding pedestal 18. Preferably, pedestal 18 includes a bore 20 through its longitudinal axis to provide for the passage of a light beam as will be explained in further detail below. The pedestal and support arms may be fabricated from any suitable metal, preferably one which exhibits good heat conductivity and a low ion milling rate.

As shown, preferably each support arm 12 includes a first portion or segment 120 which extends generally laterally away from pedestal 18, a second upstanding portion or segment 122, and a third portion or segment 124 which extends generally laterally back toward the center axis of pedestal 18. In this manner, support arm 12 holds specimen 10 a predetermined spaced distance away from pedestal 18 but generally centered over bore 20. Of course it will be apparent to those skilled in this art that the particular configuration or number of the segments or portions of the support arms or arms is not critical. What is important is that the support arm is designed to position the specimen a spaced distance away from the pedestal to provide for line-of-sight clearance for the ion gun arrangement and to permit the ion beam or beams to impinge upon both sides of the specimen.

Small recesses 14 are provided adjacent the tips of support arms 12 in portion 124. The recesses are of a depth slightly less than the typical thickness of a specimen 10 (e.g., 100–200 μm). Further, the recesses have a diameter slightly greater than the diameter of the specimen so that the specimen will seat in those recesses.

In the embodiment of the invention shown in FIGS. 1a and 1b, specimen 10 is seated on support arms 12 using a wax compound 16. Preferably, wax 16 is a relatively low melting point wax, preferably having a melting point less than about 150° C., and most preferably having a melting point in the range of from about 110° C. to 140° C. Waxes having melting points in the lower end of the range are most preferred as less heating is required to soften or melt them. The use of a wax aids in heat transfer between specimen 10 and support arms 12 to carry heat away from the specimen during milling and to reduce ion beam induced heat damage effects on the specimen.

Specimen 10 is seated in recesses 14 as follows. The wax is blended with a volatile solvent such as, for example, acetone, and the blend is applied to the recesses 14. The solvent is permitted to evaporate; optionally, the specimen holder may be heated to aid in driving off the solvent. After the wax is cooled and solidified, a specimen 10 is placed over the wax in alignment with recesses 14. The specimen holder is then reheated to cause the wax 16 to soften or melt, permitting specimen 10 to become seated in recesses 14. The wax is then cooled again, this time securing specimen 10 in position on the support arms 12.

Figure 2A:
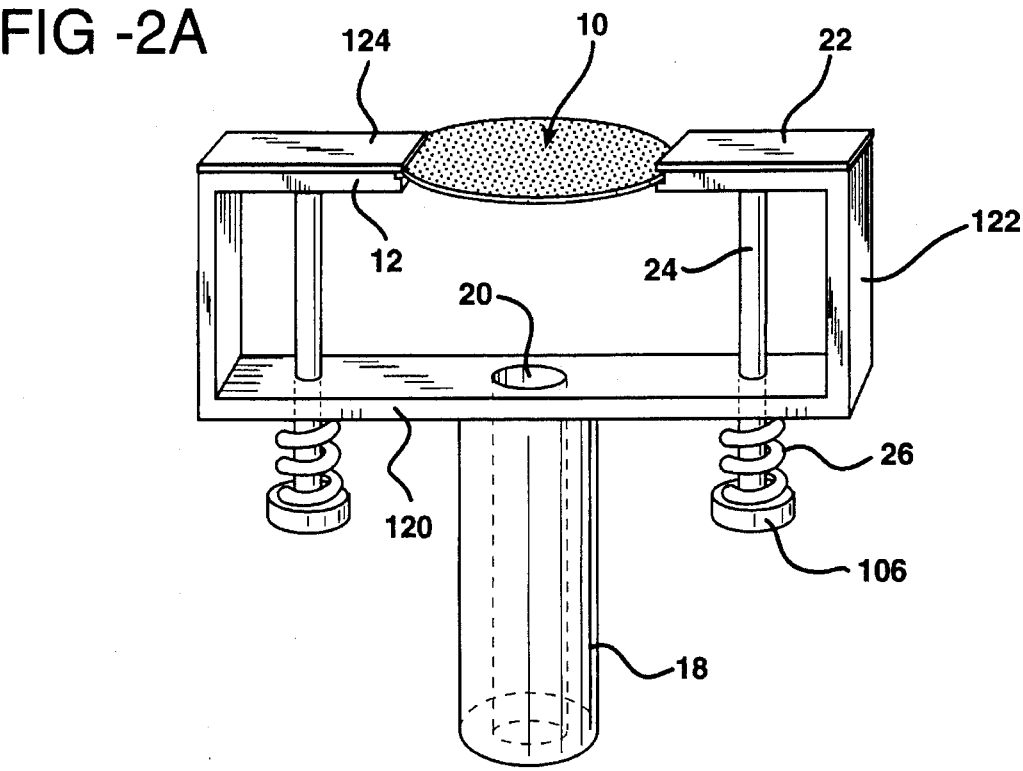
FIG. 2a is a perspective view of a two support arm embodiment of the present invention which secures the specimen with a spring-loaded clamping mechanism.
Figure 2B:
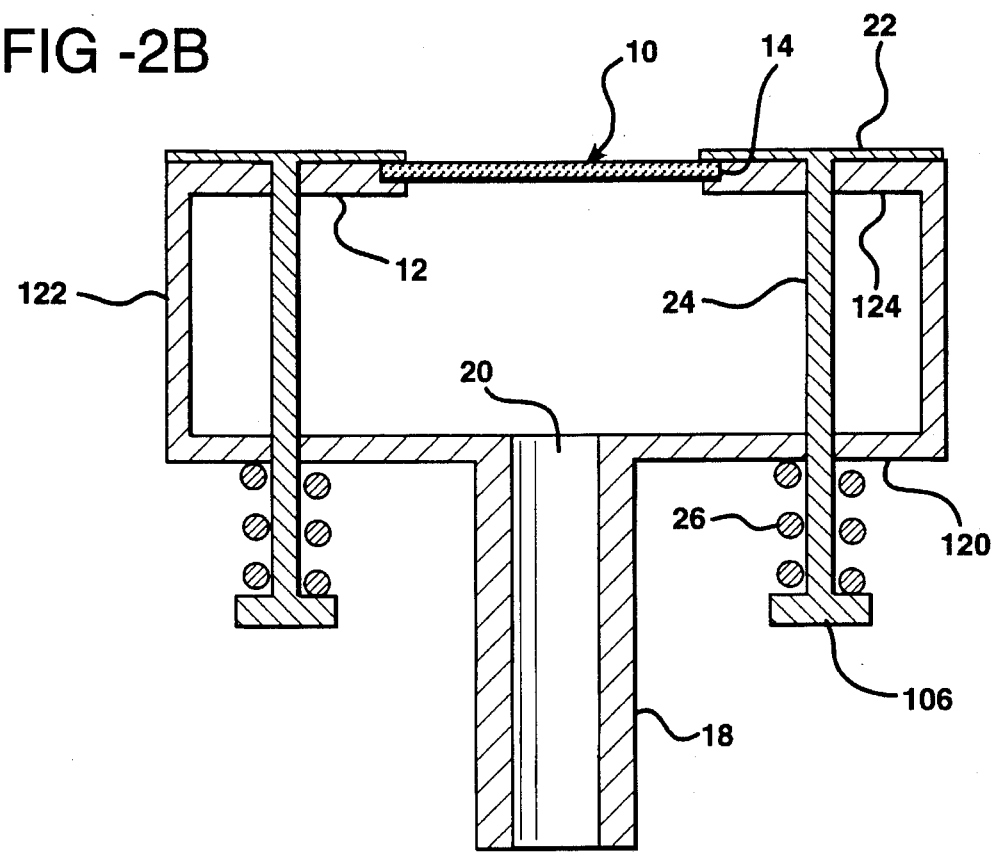

Mechanical securing means for securing specimen 10 to support arms 12 are illustrated in FIGS. 2a and 2b, 4a, and 4b. Referring now to FIGS. 2a and 2b, specimen 10 is seated on support arms 12 in recesses 14. A clamping mechanism which includes a clamping surface 22, a clamping post 24, and a spring 26 holds the peripheral edges of specimen 10 in recesses 14. As shown, each clamping surface 22 extends over the upper peripheral edge of specimen 10 to secure the specimen in recesses 14. Clamping post 24 extends through first and third portions 120 and 124, respectively of support arm 12. One end of clamping post 24 is secured to clamping surface 22 while the opposite end includes a flange 106. Between flange 106 and third portion 124 of support arm 12, spring 26 is captured. Spring 26 is sized to exert a clamping pressure on clamping surface 22. Further, springs 26 on either support arm 12 can be compressed to release clamping surface 22 for removal and insertion of different specimens as needed.

Figure 4A:
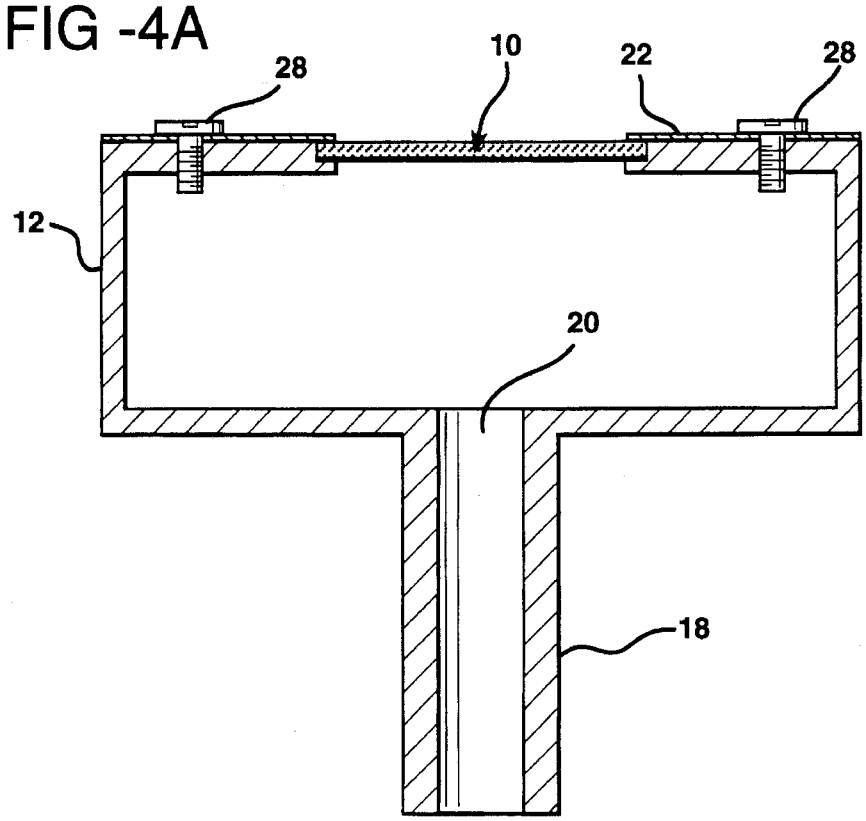
FIG. 4a is a cross-sectional view of a two support arm embodiment of the present invention which secures the specimen using screws.

In another modification of a mechanical clamping mechanism, FIG. 4a illustrates a screw 28 holding clamping surface 22 in position over specimen 10. By turning screw 28, pressure on clamping surface 22 can be released for insertion and/or removal of a specimen 10, and can be increased to secure the specimen in place.

Figure 4B:
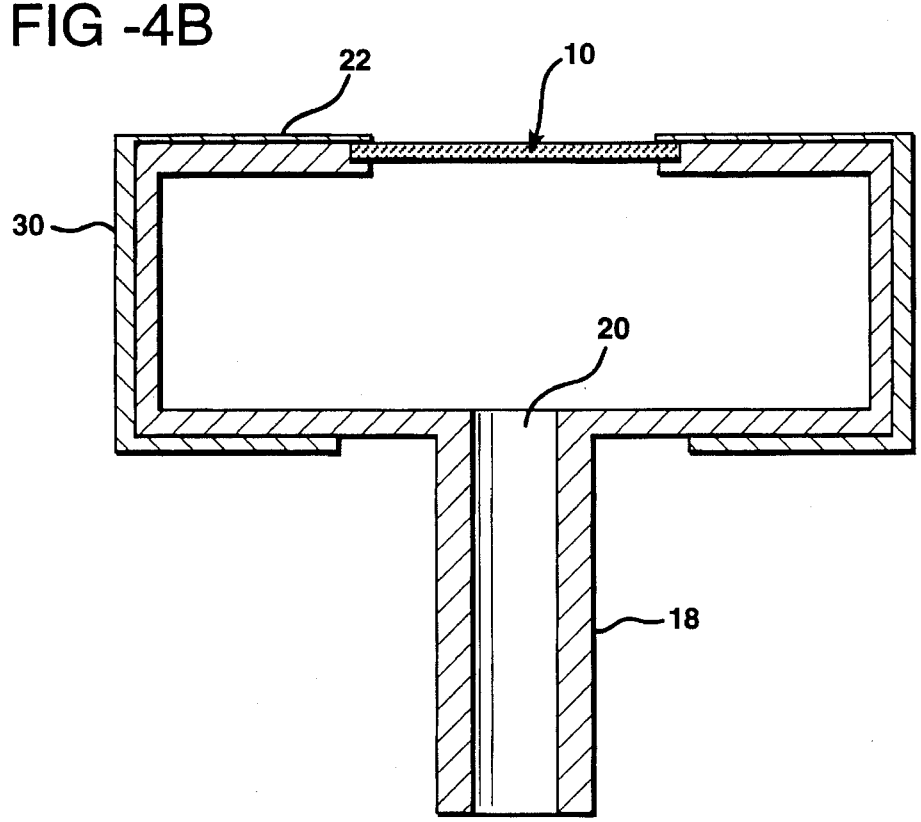
FIG. 4b is a cross-sectional view of a two support arm embodiment of the present invention which secures the specimen using C-shaped clamps.

FIG. 4b illustrates yet another form of a mechanical clamping mechanism. As there illustrated, C-shaped clamps 30 having clamping surfaces 22 are designed to snugly fit over support arms 12 to provide a clamping force on specimen 10. C-shaped clamps 10 may be slid on and off of support arms 12 to permit specimens to be insert or removed as required.

Figure 3A:
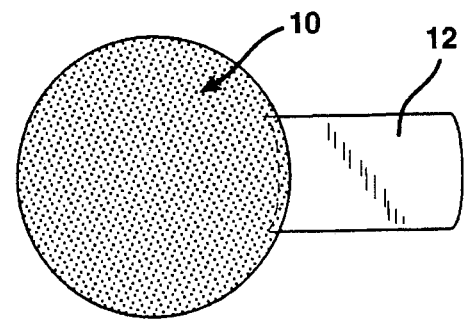
FIGS. 3a, 3b, and 3c are schematic top views of one, three, and four support arm embodiments of the invention.
Figure 3B:
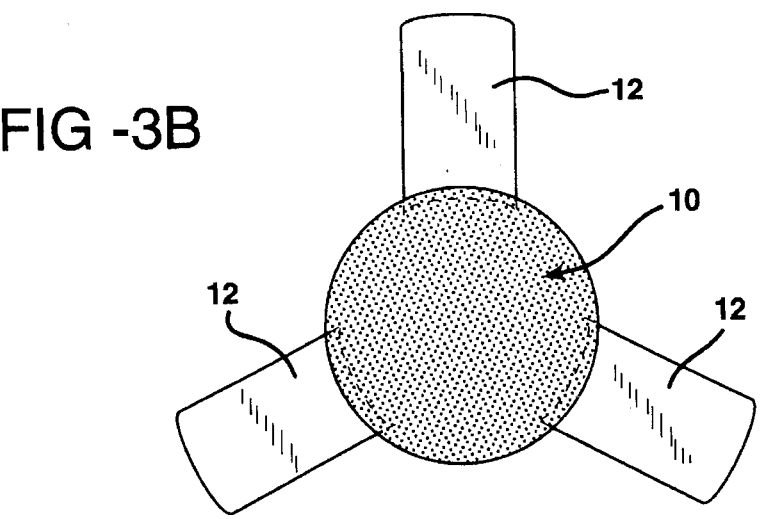
Figure 3C:
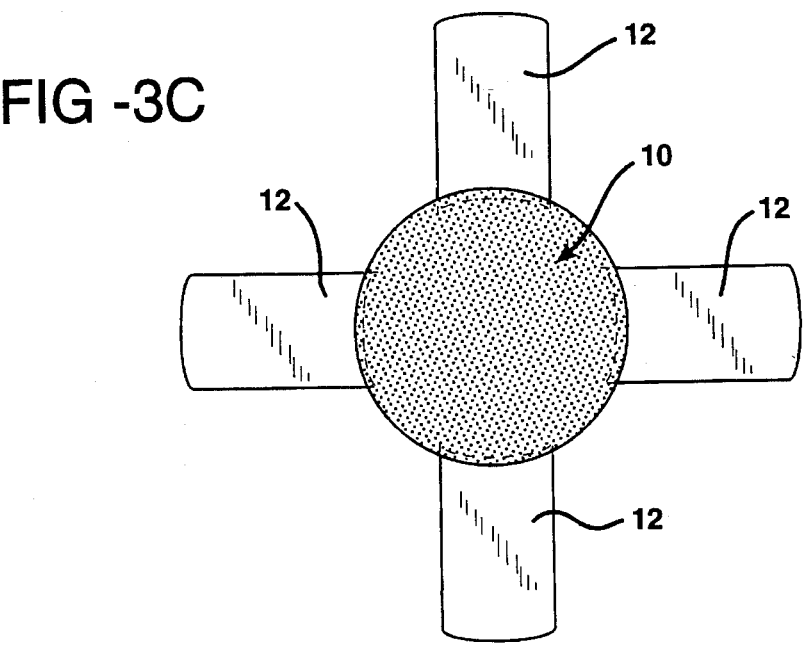

While the specimen holder of the present invention may take the form of a pair of opposing support arms as shown in FIGS. 1a, 1b, 2a, 2b, 4a, and 4b, in some instances, a single support arm 12 as shown in FIG. 3a may provide sufficient support to specimen 10 for an ion beam milling operation. Alternatively, three or four support arm embodiments of the invention are also possible as shown in FIGS. 3b and 3c, respectively.

Thus, a particular advantage of the present invention is its flexibility of design for various applications and ion milling operations. The angles between support arms may be symmetrical or non-symmetrical as desired depending upon the configuration of the ion milling guns used to mill the specimens. However, it is important that at least some portion or portions of the peripheral edges of the specimen remain unrestrained by the securing means to provide direct line-of-sight access to both major surfaces of the specimen. That is, due to the spacing of the support arm or arms from the pedestal, the ion gun or guns may be positioned at very low angles of incidence down to 0° to the specimen without striking either the pedestal or the support arms. The specimen holder of the present invention is quite suited for use in an ion beam milling system using modulated ion beams for sector ion milling. Such a system is commercially available from Gatan, Inc. of Pleasanton, Calif.

Figure 5:
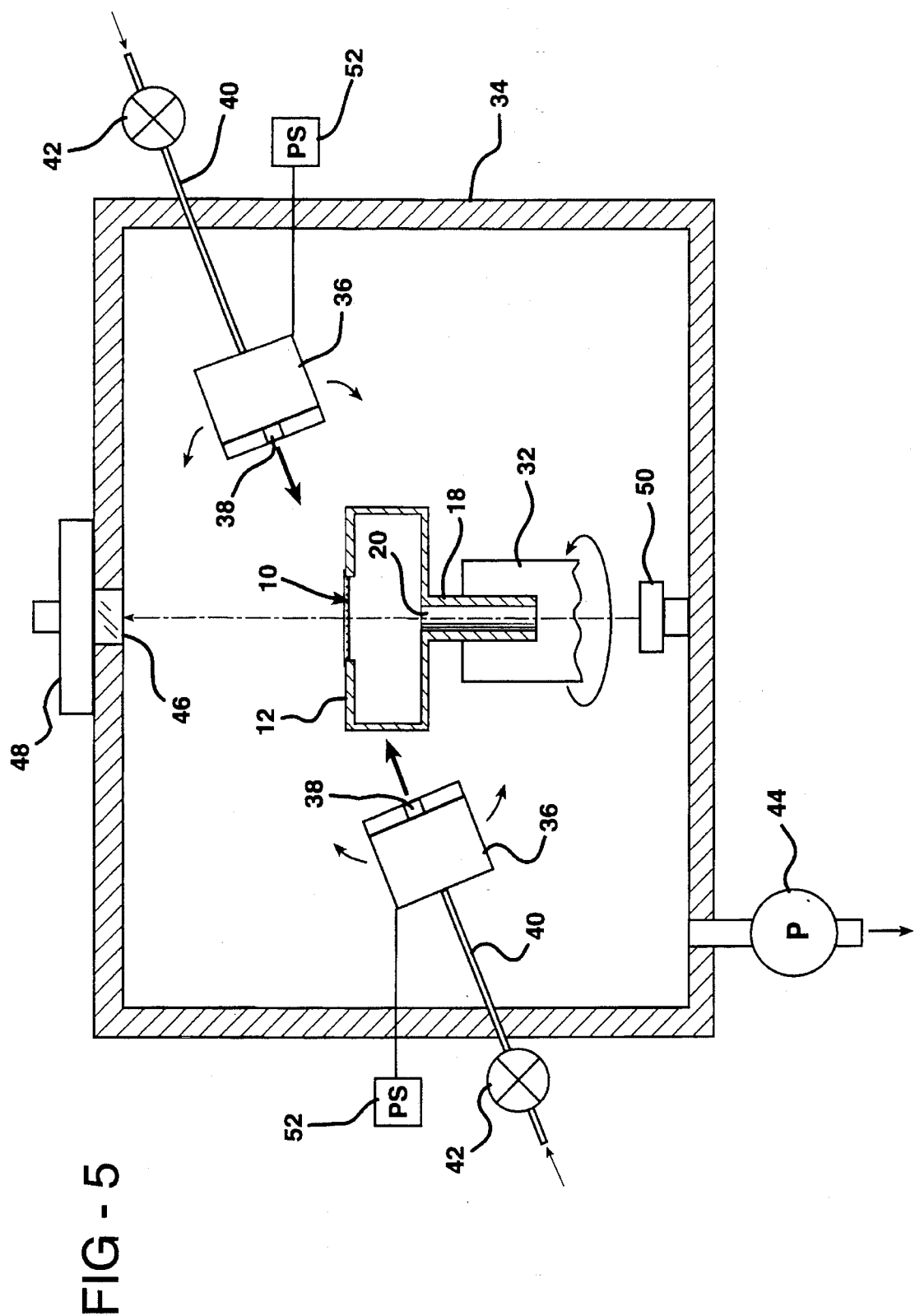
FIG. 5 is a schematic, cross-sectional view of an ion beam milling apparatus incorporating the specimen holder of the present invention.

An example of an ion beam milling system using the specimen holder of the present invention is shown in FIG. 5. As shown, specimen 10 is supported by support arms 12 of the specimen holder in vacuum chamber 34. Suitable means, such as a high vacuum pump 44 capable of reducing the pressure in chamber 34 to $10^{-6}$ Torr, are used to evacuate the chamber. The pedestal 18 of the specimen holder is fitted onto a holder mount 32. Holder mount 32 may be rotated, by suitable rotary drive means (not shown), to cause specimen 10 to rotate during ion milling. Support arms 12 position specimen 10 so that it is generally centered over bore 20.

A pair of ion guns 36 of substantially identical construction are connected to power supplies 52. In the configuration illustrated (where angles are exaggerated for simplification), one ion gun is positioned above the surface of specimen 10 and one is positioned below to direct an ion beam against the lower surface of specimen 10. A gas, typically argon, is supplied to ion gun 36 through gas supply line 40, the supply of gas being regulated by valve 42. Ion gun 36 produces a beam of energetic particles which impinges onto specimen 10 through front aperture 38. The angle between the specimen surface (either upper or lower) and the ion beams being directed from either gun 36 may be adjusted to various values down to 0° for simultaneous milling of both surfaces.

A light source 50, such as, for example a light emitting diode (LED), projects light generally vertically through pedestal bore 20. Milling may be terminated when the surface of specimen 10 is perforated or just prior to perforation when the surface of specimen 10 is sufficiently transparent so that the light from source 52 passes through specimen 10 and window 46 and impinges on a photodetector 48. Photodetector 48 may be connected through suitable circuitry (not shown) to terminate the power to ion guns 36 when it detects a predetermined threshold of light.

Sector ion milling may be carried out by controlling power to the ion guns 36 such that power is supplied whenever the specimen holder is rotated to a position where there is line-of-sight clearance to the surface of specimen 10 and power is terminated whenever, due to rotation, support arms 12 enter the path of the ion beams. This reduces specimen contamination from sputtering of metal from either the support arms or the pedestal, reduces heat input, and provides high quality specimens for analysis.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A specimen holder for two-sided ion beam milling comprising:

a pedestal having at least one extending specimen support arm adapted to engage a peripheral edge of a specimen having first and second major surfaces such that at least a portion of said peripheral edge of said specimen remains unrestrained by said support arm and spaced from said pedestal; and means for securing said specimen to said at least one specimen support arm.

2. A specimen holder as claimed in claim 1 including a plurality of specimen support arms extending from said pedestal.

3. A specimen holder as claimed in claim 1 including multiple specimen support arms extending from said pedestal.

4. A specimen holder as claimed in claim 1 in which said at least one specimen support arm includes a recess therein for engaging said peripheral edge of said specimen, the depth of said recess being less than the height of said specimen.

5. A specimen holder as claimed in claim 1 in which said securing means comprise wax.

6. A specimen holder as claimed in claim 5 in which said wax is a low melting point hydrocarbon wax.

7. A specimen holder as claimed in claim 4 in which said securing means comprise wax, and said wax is disposed in said recess.

8. A specimen holder as claimed in claim 1 in which said securing means is a clamp.

9. A specimen holder as claimed in claim 8 in which said clamp includes a clamping surface for engaging said peripheral edge of said specimen, a post extending from said clamping surface, and a spring on said post for biasing said clamping surface against said specimen support arm.

10. A specimen holder as claimed in claim 1 in which said securing means comprises a clamping surface for engaging said peripheral edge of said specimen and a set screw extending through said clamping surface for securing said clamping surface to said specimen support arm.

11. A specimen holder as claimed in claim 1 in which said securing means comprises a C-shaped clamp having a clamping surface for engaging said peripheral edge of said specimen and a base portion extending around and securing said clamp to said specimen support arm.

12. A specimen holder as claimed in claim 1 in which said pedestal has a bore therethrough.

13. A specimen holder as claimed in claim 1 in which said at least one specimen support arm includes a first portion which extends laterally away from said pedestal, a second upstanding portion, and a third portion extending laterally toward said pedestal.

14. A specimen holder as claimed in claim 13 including a recess in said third portion of said at least one support arm for engaging said peripheral edge of said specimen, the depth of said recess being less than the height of said specimen.

15. A specimen holder as claimed in claim 13 including a plurality of specimen support arms extending from said pedestal.

16. A specimen holder as claimed in claim 13 including multiple specimen support arms extending from said pedestal.

17. An apparatus for two-sided ion beam milling comprising:

a vacuum chamber and means for providing a vacuum within said chamber;

a specimen holder within said chamber for holding a specimen to be milled;

a plurality of ion guns within said chamber, at least one of said guns positioned to provide an ion beam to a first side of said specimen and at least one other of said guns positioned to provide an ion beam to a second side of said specimen, said plurality of guns be adjustable to provide very low milling angles of incidence down to 0°.

18. An apparatus as claimed in claim 17 in which said specimen holder comprises a pedestal having at least one extending specimen support arm adapted to engage a peripheral edge of said specimen such that at least a portion of said peripheral edge of said specimen remains unrestrained by said support arm and spaced from said pedestal; and means for securing said specimen to said at least one specimen support arm.

19. An apparatus as claimed in claim 18 including a plurality of specimen support arms extending from said pedestal.

20. An apparatus as claimed in claim 18 in which said at least one specimen support arm includes a recess therein for engaging said peripheral edge of said specimen, the depth of said recess being less than the height of said specimen.

21. A method for the two-sided ion beam milling of specimens comprising the steps of:

providing a specimen having first and second major surfaces and a peripheral edge to be milled to a vacuum chamber and securing said specimen such that at least a portion of said peripheral edge remains unrestrained, evacuating said chamber to form a vacuum therein, and ion milling said specimen using a milling angle down to 0°.

22. A method as claimed in claim 21 including the step of simultaneously milling said specimen on both major surfaces thereof.

23. A method as claimed in claim 21 including the step of rotating said specimen during ion milling.

24. A method as claimed in claim 23 wherein said specimen is secured by a support holder having at least one extending specimen support arm and wherein said ion milling is carried out by a plurality of ion guns, said method including the step of terminating power to said ion guns whenever said support arm is rotated into the path of ion beams emanating from said ion guns.

* * * * *

UNITED STATES PATENT AND TRADEMARK OFFICE
CERTIFICATE OF CORRECTION

PATENT NO. : 5,472,566
DATED : December 5, 1995
INVENTOR(S) : Swann et al.

It is certified that error appears in the above-indentified patent and that said Letters Patent is hereby corrected as shown below:

Col. 7, Line 54, "set screw" should be --screw--.

Signed and Sealed this

Twenty-sixth Day of March, 1996

Attest:

BRUCE LEHMAN

Attesting Officer     Commissioner of Patents and Trademarks